(12) United States Patent
Krenzel

(10) Patent No.: US 9,044,324 B2
(45) Date of Patent: Jun. 2, 2015

(54) SELECTIVELY ADJUSTABLE ARM AND SHOULDER SUPPORT

(76) Inventor: Ronald Louis Krenzel, Longmont, CO (US)

(*) Notice: Subject to any disclaimer, the term of this patent is extended or adjusted under 35 U.S.C. 154(b) by 509 days.

(21) Appl. No.: 13/306,285

(22) Filed: Nov. 29, 2011

(65) Prior Publication Data

US 2012/0143109 A1 Jun. 7, 2012

Related U.S. Application Data

(60) Provisional application No. 61/419,044, filed on Dec. 2, 2010.

(51) Int. Cl.
*A61F 5/00* (2006.01)
*A61F 13/00* (2006.01)
*A61F 5/37* (2006.01)

(52) U.S. Cl.
CPC .................................... *A61F 5/3738* (2013.01)

(58) Field of Classification Search
CPC ....... A61F 5/37; A61F 5/3738; A61F 5/3723; A61F 5/3753; A61F 5/05858; A61F 5/058; A61F 5/3776; A61F 5/3784; A61M 5/52
USPC ............ 602/4, 20, 60–62, 5, 19, 21; 2/44, 45, 2/24; 128/869, 876, 877; 224/158, 162
See application file for complete search history.

(56) References Cited

U.S. PATENT DOCUMENTS

| | | | | |
|---|---|---|---|---|
| 890,842 | A | * | 6/1908 | Cheatham .......................... 602/4 |
| 1,267,142 | A | * | 5/1918 | Stowers et al. .................... 602/4 |
| 1,304,153 | A | * | 5/1919 | Bugge ............................... 602/4 |
| 2,187,323 | A | | 1/1940 | Kelton et al. |
| 2,358,551 | A | | 9/1944 | Beaton |
| 3,000,378 | A | | 9/1961 | Zieman |
| 3,338,236 | A | | 8/1967 | McLeod, Jr. |
| 3,404,680 | A | | 10/1968 | Guttman et al. |
| 3,815,588 | A | | 6/1974 | Klausner |
| 4,188,944 | A | | 2/1980 | Augustyniak |
| 4,598,703 | A | | 7/1986 | Lindemann |
| 4,716,895 | A | | 1/1988 | Marques et al. |
| 4,751,923 | A | * | 6/1988 | Marino ............................ 602/4 |
| 4,834,082 | A | | 5/1989 | Ghadiali |
| 5,086,762 | A | * | 2/1992 | Chee ............................... 602/4 |
| 5,203,763 | A | | 4/1993 | Lajiness-O'Neill |
| 5,358,470 | A | | 10/1994 | Johnson |
| 5,358,471 | A | | 10/1994 | Klotz |

(Continued)

FOREIGN PATENT DOCUMENTS

| | | |
|---|---|---|
| DE | 3936232 | 5/1991 |
| EP | 0198482 | 4/1986 |

OTHER PUBLICATIONS

SupportsUSA, shoulder supports, arm slings and immobilizers; www.supoortsusa.com/arm/shoulder; Mar. 11, 2003; 3 pages.

(Continued)

*Primary Examiner* — Kim M Lewis
(74) *Attorney, Agent, or Firm* — Sheridan Ross P.C.

(57) ABSTRACT

A contouring arm and shoulder support is provided that is secured to a supporting and stabilizing belt. The support is interconnected to the belt by an adjustable shoulder component that supports an adjustable arm cuff and provides upward force that moves the patient's shoulder joint out of subluxation.

17 Claims, 8 Drawing Sheets

(56) References Cited

U.S. PATENT DOCUMENTS

| | | | |
|---|---|---|---|
| 5,403,268 A | | 4/1995 | Clement |
| 5,520,620 A | | 5/1996 | Johnson |
| 5,538,499 A | * | 7/1996 | Schwenn et al. ............ 602/20 |
| 5,558,626 A | | 9/1996 | Holtzman et al. |
| 5,628,725 A | | 5/1997 | Ostergard |
| 5,682,653 A | | 11/1997 | Berglof et al. |
| 5,857,990 A | | 1/1999 | Maas |
| 5,867,826 A | | 2/1999 | Wilkinson |
| 6,099,489 A | | 8/2000 | Herzberg et al. |
| 6,106,493 A | | 8/2000 | Rozell |
| RE36,869 E | | 9/2000 | Ewen |
| 6,292,985 B1 | | 9/2001 | Grunberger |
| 6,421,834 B2 | | 7/2002 | Kester |
| 6,464,656 B1 | | 10/2002 | Salvucci et al. |
| 6,837,862 B2 | | 1/2005 | Driver |
| 6,945,945 B2 | | 9/2005 | Givler et al. |
| 6,979,303 B2 | * | 12/2005 | Jestrabek-Hart ............ 602/4 |
| 7,789,114 B2 | | 9/2010 | Pace et al. |
| 8,109,273 B2 | | 2/2012 | Golden et al. |
| 8,196,588 B1 | | 6/2012 | Krenzel |
| 2002/0007133 A1 | * | 1/2002 | Givler et al. ............ 602/20 |
| 2005/0273026 A1 | | 12/2005 | Howard |
| 2007/0129657 A1 | * | 6/2007 | Fisher ............ 602/4 |

OTHER PUBLICATIONS

Frank Stubbs, Inc.; www.fstubbs.com/noflash/orthooedic/324.htm; Dec. 1, 2003; 1 page.
Manor Drug Store; vvvw.manordrug.com/FLA/fla/products/28-911.htm; Dec. 1, 2003; 1 page.
Therafin Corporation; www.therafin.com/armposition.htm; Feb. 27, 2004; 2 pages.
Ambroise, The Wilmer® Carrying Orthosis; Wilmer® Carrying Orthosis for Brachial Plexus; www.ambroise-uk.com/carryingOrthosis.htm; Mar. 26, 2003; 1 page.
Dalco Arm Slings; www.dalcointernational.com/Dalco_Arm_Slings.html; Feb. 4, 2003; 2 pages.
Arm Slings: Universal Shoulder Immobilizer—FastHealth Sports Injury Store; www.fasthealth.com/store/motion/ortho-12-4129.php; Apr. 4, 2003; 1 page.
SupportsUSA; Super Sling—Universal Shoulder Immobilizer; http://supports4less.comfbirdcronin/shouldersupports/superslingshoulderimmobilizer.htm; Feb. 4, 2003; 1 page.
SupportsUSA; Sling and Swathe Shoulder Immobilizer; http://supports4less.com/birdcronin/shouldersupports/slingswatheshoulderimmobilizer.htm; Feb. 4, 2003; 1 page.
SupportsUSA; Comfor™ Shoulder Immobilizer• Universal; http://supports4less.com/birdcronin/shouldersupports/comforuniversal•shoulderimmobilizer . . . ; Feb. 4, 2003; 1 page.
SupportsUSA; Bicro™ Shoulder Immobilizer; http://supports4less.com/birdcronin/shouldersupports/bicroshoulderimmobilizer.htm; Feb. 4, 2003; 1 page.
Royce Medical®; Orthopaedic Supplies; Arm Slings; Shoulder Immibilizers; Clavicle Supports, et al., date unknown, 1 page.
Joslin Orthopedic Gear; The Ultimate Arm Sling®; Arm Sling Design; www.armsling.com/design.htm; Feb. 8, 2003; 2 pages.
Donjoy; UltraSling® ER; Introducing the Revolutionary UltraSling® External Rotation, date unknown, 1 page.
Bird & Cronin, Inc.; 4 pages of various Slings, Shoulder Immobilizers; Therapy Wraps, etc.; 1-800-328-1095, date unknown.
Professional Products, Inc.; R000333 A/K; The Six Shooter; 2001, 1 page.
BREG; Neutral Wedge; date unknown, 2 pages.
"DonJoy Shoulder Cradle," DJO Global, 2014, [retrieved on Feb. 25, 2014], 3 pages. Retrieved from: www.djoglobal.com/products/donjoy/donjoy-shoulder-cradle.
"GivMohr® Sling," Patterson Medical Holdings, Inc., 2014, 1 page.
"Lerman Shoulder," DJO Global, 2014, [retrieved on Feb. 25, 2014], 1 page. Retrieved from: www.djoglobal.com/products/donjoy/lerman-shoulder.
"S.C.O.I. Shoulder Brace,"DJO Global, 2014, 1 page.

* cited by examiner

SELECTIVELY ADJUSTABLE ARM AND SHOULDER SUPPORT

This application claims the benefit of U.S. Patent Application Ser. No. 61/419,044, filed Dec. 2, 2010, the entire disclosure of which is incorporated by reference herein.

FIELD OF THE INVENTION

Embodiments of the present invention generally relate to a device that supports and selectively positions a patient's arm. More specifically, the contemplated support maintains the patient's shoulder in such a way to prevent or reduce the amount of shoulder subluxation.

BACKGROUND OF THE INVENTION

Stroke and neurological injuries are difficult and costly problems. Four out of every five American families will be impacted by stroke and four million Americans currently live with its lingering effects, making stroke the leading cause of serious, long-term adult disability in the United States. Further the approximately 795,000 people who suffer stroke each year in the United States approximately 144,000 die, 185,000 are recurrent attacks, and 466,000 are new cases. An estimated 33% of stroke survivors need help caring for them and 70% cannot return to their previous occupations. According to research by the American Heart Association (AHA) and Centers for Disease Control (CDC), the estimated 2009 direct and indirect cost to cover inpatient care, rehabilitation, and follow-up care for lasting deficits of a stroke was $68.9 billion (numbers converted to 1999 dollars using the medical component of CPI). In 2010 the effects of a stroke alone are projected to cost the United States nearly $73.7 billion.

Given the number of affected persons and considerable cost for their care, much work has been done to identify clinical practices yielding the most satisfactory outcomes for glenohumeral subluxations (GHS). This research has found that proactive, early intervention to support and stabilize the shoulder complex is critical for two reasons: 1) proper biomechanical positioning reduces secondary damage to the shoulder joint and capsule and 2) proper support and positioning ameliorates pain. Clinical therapists report that pain is a primary obstacle they face when implementing rehabilitative techniques for the upper extremity. Understandably, patients in pain are mentally distracted, unable to remain positive about their situations, and obviously hindered in participating in recommended therapeutic regimes. Conquering pain becomes yet another task on the tortuous path to stroke recovery; thus, tools that help ameliorate pain and maintain the integrity of the shoulder capsule are of critical importance to the occupational therapist.

Hemiplegic shoulder pain (HSP) and shoulder subluxation, i.e., a partial or complete dislocation, are common complications after a stroke or other neurological injury. Shoulder pain can begin as early as 2 weeks post stroke and results in significant long-term disability that impedes rehabilitation intervention, and limits the patient's ability to reach their maximum functional potential. Shoulder subluxations affect up to 81% of patients with hemiplegic shoulder pain and often occur during a "flaccid stage" of stroke recovery, i.e., wherein the patient suffers severe sensory loss rendering the patient's arm limp and floppy. Improper positioning of the shoulder and lack of support of the upper arm when in an upright position can contribute to subluxation, which aggravates shoulder pain and other secondary shoulder injury or stroke complications. For the majority of occupational therapists, proactively managing shoulder pain and implementing effective biomechanical joint positioning to compensate for lost muscle tone in the upper arm is critical to increase tolerance for other neuro-rehabilitative techniques and to maintain normal length of surrounding muscle/soft tissue. Most occupational therapists use supports, slings, strapping or functional electrical stimulation for the early intervention of GHS, but traditional apparatus are in some instances ineffective.

Several slings and arm support systems have been developed to help stabilize the shoulder complex. Examples include the Omo Nuerexa (Otto Bock®, Minneapolis Minn.), the GivMohr® Sling (GivMohr Corp., Albuquerque N. Mex.), and the Arm Escort (Maddak®, Wayne N.J.). Shoulder slings generally employ a cradle that receives the lower part of the arm. A strap is attached at one end of the cradle, is looped around the neck of the user, and is attached to another end of the cradle to maintain the arm in a desired position. The length of a strap in a typical sling may be adjusted to allow the lower arm to be positioned within a certain range of angles relative to the upper arm. In general, as the length of the strap is increased, the position of the lower arm relative to the torso is lowered, but the range of positions is limited by the structure of the sling itself.

While effective in some circumstances, simple slings and other similar devices have not been widely accepted for several reasons: 1) complicated strapping arrangements make donning difficult, particularly for the elderly, those with cognitive deficits, and those who lack caregiver support; 2) the devices effectively suspend the arm at or just proximal to the hand, and do not provide adequate support while seated, which can comprise a substantial portion of the user's day; 3) the devices cover or encapsulate large regions of the shoulder, arm, and hand, interfering with natural thermal regulation and making the patient uncomfortable; and 4) the strap applies pressure across the user's ipsilateral trapezius or contralateral axillary region, causing additional pain, skin breakdown, or muscle pathologies. One of skill in the art will appreciate that slings can potentially exacerbate their injury by immobilizing the distal arm that causes internal humeral rotation, which is an ideal position for protecting suture lines, but promotes anterior subluxations. Furthermore, existing sling designs promote proper alignment of only parts of the upper arm when the entire arm should have support in the form of shoulder protraction, humeral external rotation with abduction and flexion, forearm supination, neutral wrist, extended fingers, and thumb abduction.

To address the deficiencies of the prior art, therapists frequently fabricate less-than-ideal support systems from materials found in their facilities such as pillows, towels and foam wedges. Further, patients often make do with slings that only partially support the arm in one position (sitting or standing).

Within the upper-limb rehabilitation field there exists a recognized need for new arm support options, particularly ones that are comfortable that are intuitive and easy to use, can be readily donned (preferably independently by the patient), can reduce pain, can promote proper entire arm alignment, are compatible with other treatment interventions, and offer greater dynamic support when sitting, standing and ambulating.

The following disclosure describes an improved support that maintains the patient's arm in a predetermined position and that elevates the head of the patient's humerus into the shoulder socket to reduce pain and secondary damage. The contemplated support also addresses the issues outlined above and other issues understood by those of skill in the art.

SUMMARY OF THE INVENTION

It is one aspect of the present invention to provide an arm and shoulder support. More specifically, an arm and shoulder support is provided that maintains a patient's arm in a predetermined position and that prevents or reduces shoulder subluxation. The contemplated device at least partially envelops the patient's arm and maintains it in a stable orientation.

It is one aspect of the present invention to provide an arm and shoulder support for maintaining a patient's arm and predetermined position of use. The support is comprised of various components that work in concert to urge the patient's humorous upwardly in a comfortable manner such that the head of the humerus is firmly seated within the shoulder socket. One embodiment of the present invention comprises an adjustable belt for positioning about a user's waist and an arm cuff that interconnects to the patient's forearm below the elbow. The cuff is interconnected to the belt by a strap that spans from the cuff to an attachment anchor point of the belt. The strap may be comprised of various interlock straps, one being a cushioned and selectively adjustable shoulder component that rests on the patient's shoulder and does not injure the same. Further embodiments of the present invention comprise additional features for securing the user's lower arm near the wrist and provide a grip member for the patient's hand.

The support suspends the arm at the elbow just distal to the olecranon using a structurally rigid open-cuff that prevents soft tissue damage under compression. Attached distally to the cuff is an adaptable component that supports the forearm in supination and the wrist in a neutral alignment, allowing for variable tone and ideal positioning for the distal arm. A posterior assist band may also be included to help minimize internal humeral rotation for patients who have increased muscle tone. Because the contemplated shoulder uses a different anchoring system than existing designs and provides suspension at the elbow as opposed to just the wrist/hand, it functions very well for users who are forced to spend a significant time sitting as a result of their other motor impairments. The support also allows for a more normal arm swing, which facilitates balance during ambulation, and protects the upper arm in functional transfers to/from sitting.

It is one aspect of one embodiment of the present invention to provide a shoulder support that is comfortable and easy to don, and easy to adjust. More specifically, existing strap designs support the compromised arm using ipsilateral over-the-shoulder webbing/straps positioned across the chest or contralateral shoulder auxiliary region. These arrangements do not comfortably provide the force reaction point needed to pull the humeral head posterior and superior as required for effective glenohumeral alignment; they are also more uncomfortable for women by compressing their breast(s). The device of embodiments of the present invention, thus, employ a unique adjustable belt anchor that facilitates easy donning, provides the necessary reaction point to counter anterior-inferior subluxations, and serves as a functional and comfortable gait belt. Moreover, it has been found that many stroke patients lack sufficient dexterity, strength, and bilateral coordination needed to secure common plastic belt fasteners used in existing medical products, but are able to fasten motor vehicle seat belt latches. The fastening mechanisms used in conjunction with one embodiment of the device are larger in size and are simple to operate to permit one-handed use for closure and cinching, which is an added advantage being that individuals find their use intuitive. The anchoring belt may also incorporate a contoured inner structural stay that reduces belt migration up the patient's back while providing a solid, secure attachment point for the shoulder component. The shoulder support system has been purposefully developed to be comfortable for users in wheelchairs or those who must remain seated for extended periods as well as serve as a gait belt for therapists/caregivers during functional mobility.

The belt of one embodiment of the present invention selectively receives the back strap and functions to hold the shoulder component. This aspect of embodiments of the present invention is unique as it is believed that no other subluxation device integrates a belt to achieve uniform engagement around a patient's waist. More specifically, U.S. Pat. No. 6,945,945 to Givler et al. ("Givler"), which is incorporated by reference in its entirety herein, describes a system that comprises a shoulder strap and associated elbow piece and hand grip. Givler, however, does not disclose the use of a belt for providing consistent pressure to the upper portion of the shoulder strap. Conversely, Givler interconnects one end of the shoulder strap to the patient's other shoulder, which is not ideal. Some belts of embodiments of the present invention have a moldable metal stay that contours to the patient's body and to help prevent distortion from the force generated by the tension applied by the back strap. In one embodiment of the present invention, the belt is made of foam padding and may include a non-tempered aluminum stay.

The Summary of the Invention is neither intended nor should it be construed as being representative of the full extent and scope of the present invention. Moreover, references made herein to "the present invention" or aspects thereof should be understood to mean certain embodiments of the present invention and should not necessarily be construed as limiting all embodiments to a particular description. The present invention is set forth in various levels of detail in the Summary of the Invention as well as in the attached drawings and the Detailed Description of the Invention and no limitation as to the scope of the present invention is intended by either the inclusion or non-inclusion of elements, components, etc. in this Summary of the Invention. Additional aspects of the present invention will become more readily apparent from the Detail Description, particularly when taken together with the drawings.

BRIEF DESCRIPTION OF THE DRAWINGS

The accompanying drawings, which are incorporated in and constitute a part of the specification, illustrate embodiments of the invention and together with the general description of the invention given above and the detailed description of the drawings given below, serve to explain the principles of these inventions.

Figure 1:
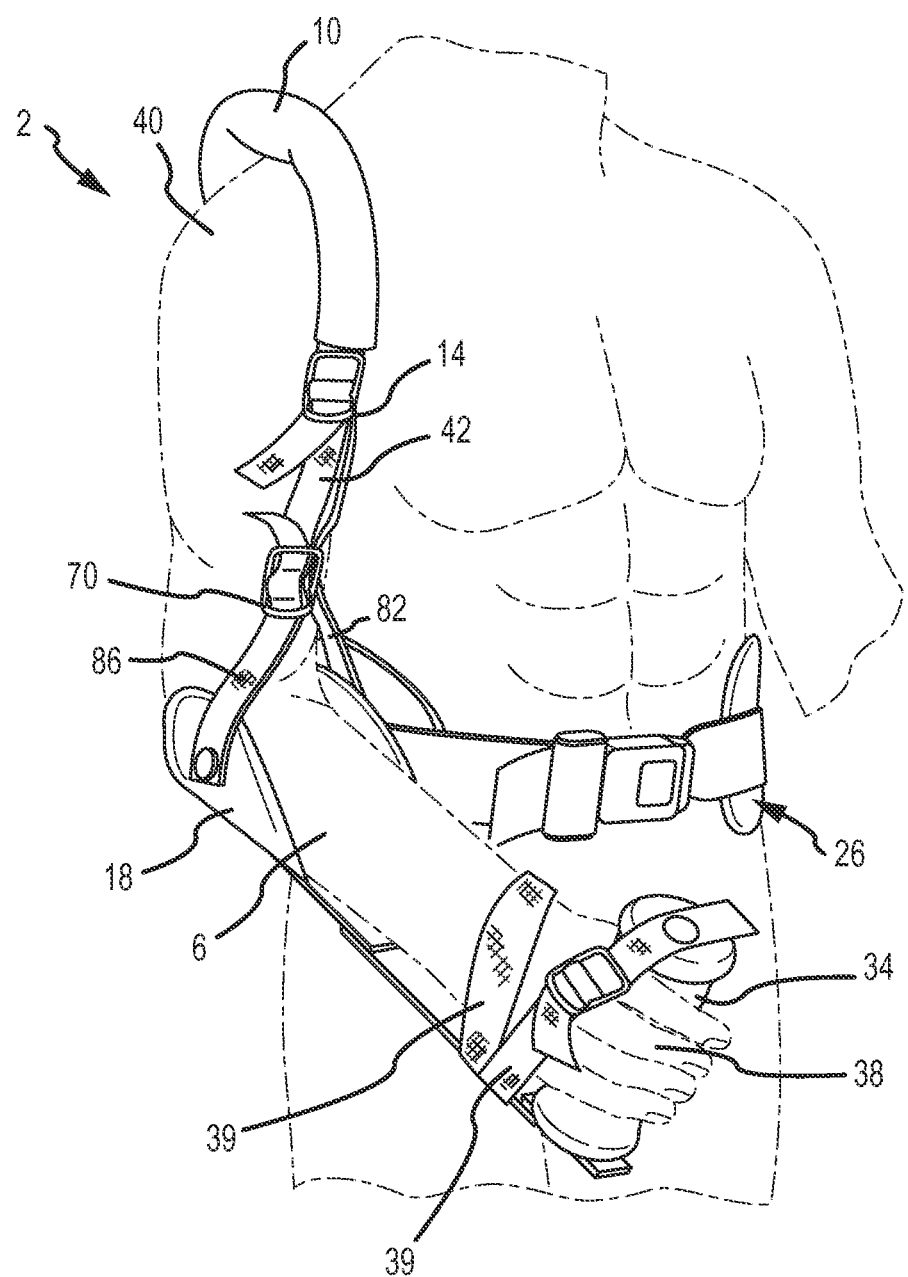
FIG. 1 is a front perspective view of a patient wearing a support of one embodiment of the present invention.
Figure 2:
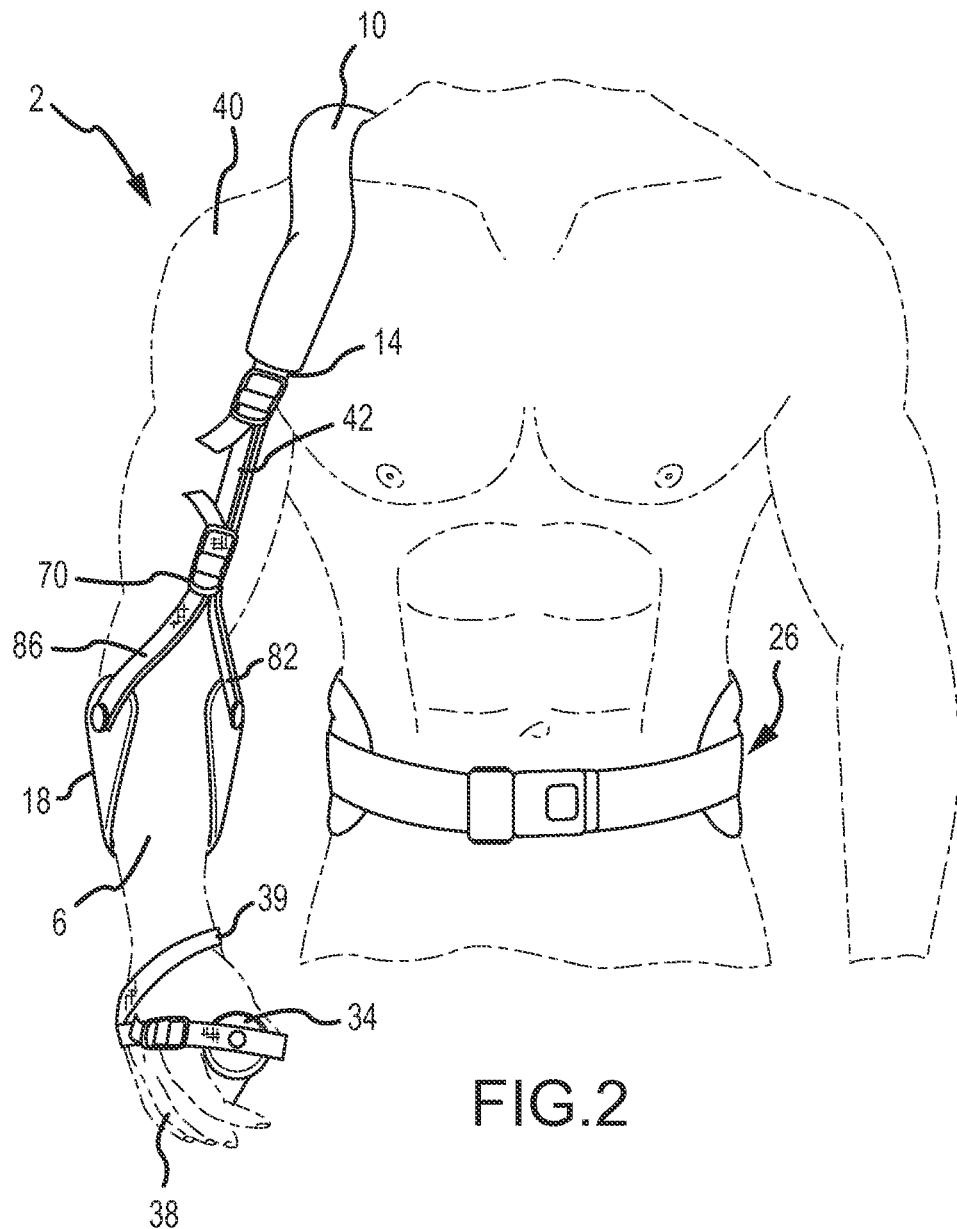
FIG. 2 is a front elevation view of FIG. 1.

To assist in the understanding of one embodiment of the present invention, the following list of components and associated numbering found in the drawings is provided herein:

| # | Component |
|---|---|
| 2 | Shoulder support |
| 6 | Arm |
| 10 | Shoulder component |
| 14 | First end |
| 16 | Adjustable strap |
| 18 | Arm cuff |
| 22 | Second end |
| 26 | Belt |
| 26O | Belt outer portion |
| 26I | Belt inner portion |
| 34 | Grip |
| 38 | Hand |
| 39 | Hand restraint |
| 40 | Shoulder |
| 42 | Front strap |
| 46 | Rear strap |
| 54 | Elbow |
| 55 | Fastening member |
| 56 | Loop material |
| 57 | Hook material |
| 58 | Core |
| 59 | Gap |
| 62 | Padding |
| 66 | Cord |
| 70 | Ladder lock |
| 74 | Indentations |
| 78 | Lower arm |
| 82 | Medial strap |
| 86 | Lateral strap |
| 90 | First rigid member |
| 94 | Second rigid member |
| 100 | Primary belt |
| 104 | Padded belt |
| 108 | First end |
| 112 | Second end |
| 114 | Buckle |
| 130 | Grasp loop |

It should be understood that the drawings are not necessarily to scale. In certain instances, details that are not necessary for an understanding of the invention or that render other details difficult to perceive may have been omitted. It should be understood, of course, that the invention is not necessarily limited to the particular embodiments illustrated herein.

DETAILED DESCRIPTION

FIGS. 1-8 show an arm and shoulder support 2 for maintaining a patient's arm 6 in a predetermined position. More specifically, one embodiment of the present invention generally comprises a shoulder component 10 that interconnects on a first end 14 to an arm cuff 18 and on a second end 22, adjacent to the patient's posterior, to an adjustable belt 26. The arm cuff 18 may be associated with a hand grip 34 that secures the patient's hand 38 with an adjustable restraint 39. The support 2 positions the patient's arm 6 such that the head of the humerus is transitioned upwardly into the shoulder socket 40, which reduces pain and facilitates rehabilitation and recovery.

An adjustable front strap 42 is used to interconnect the shoulder component 10 to the arm cuff 18. Similarly, an adjustable rear strap 46 is used to interconnect the shoulder component 10 to the belt 26. The straps allow the caregiver to customize the configuration of the support 2 to fit patient's need and body configuration. From an adjustable belt anchor point (see FIGS. 4 and 5) the rear strap 46 and shoulder component 10 traverse upwardly along the patient's back. The shoulder component 10 crosses the patient's ipsilateral scapula and is interconnected to the front strap 42, which is in turn interconnected to the arm cuff 18 that secures the patient's arm 6 adjacent to the elbow 54.

Figure 3:
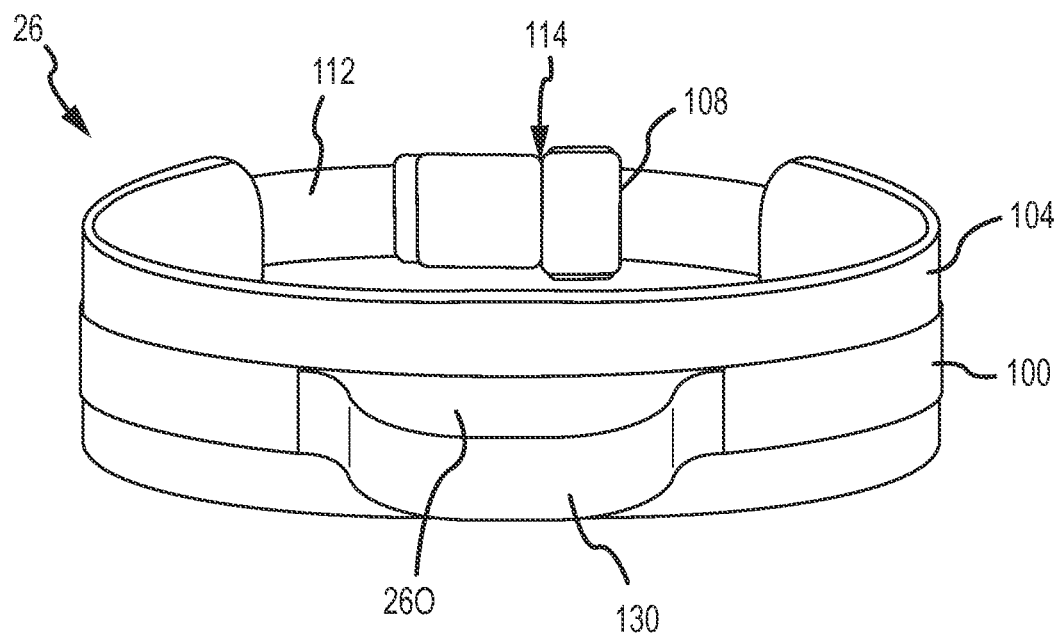
FIG. 3 is a rear perspective view showing a belt of one embodiment of the present invention.

FIG. 3 shows the belt of one embodiment of the present invention. The belt is comprised of a primary belt 100 of a first width that is interconnected to a padded belt 104 of a second width. The primary belt 100 is sewn or otherwise connected to the padded belt 104. In one alternative embodiment, however, of the present invention, the padded belt 104 is removable from the primary belt 100 to allow it to be cleaned or replaced. The primary belt 100 provides the support needed to secure the rear strap. The primary belt 100 has a first end 108 and a second end 112 that are associated with the conjoining parts of a buckle 114. In one embodiment, the buckle is similar to those commonly used for automobile seat belts, which facilitates interconnection by physically impaired individuals. The primary belt 100 is sewn or otherwise connected to the padded belt 104.

Figure 4:
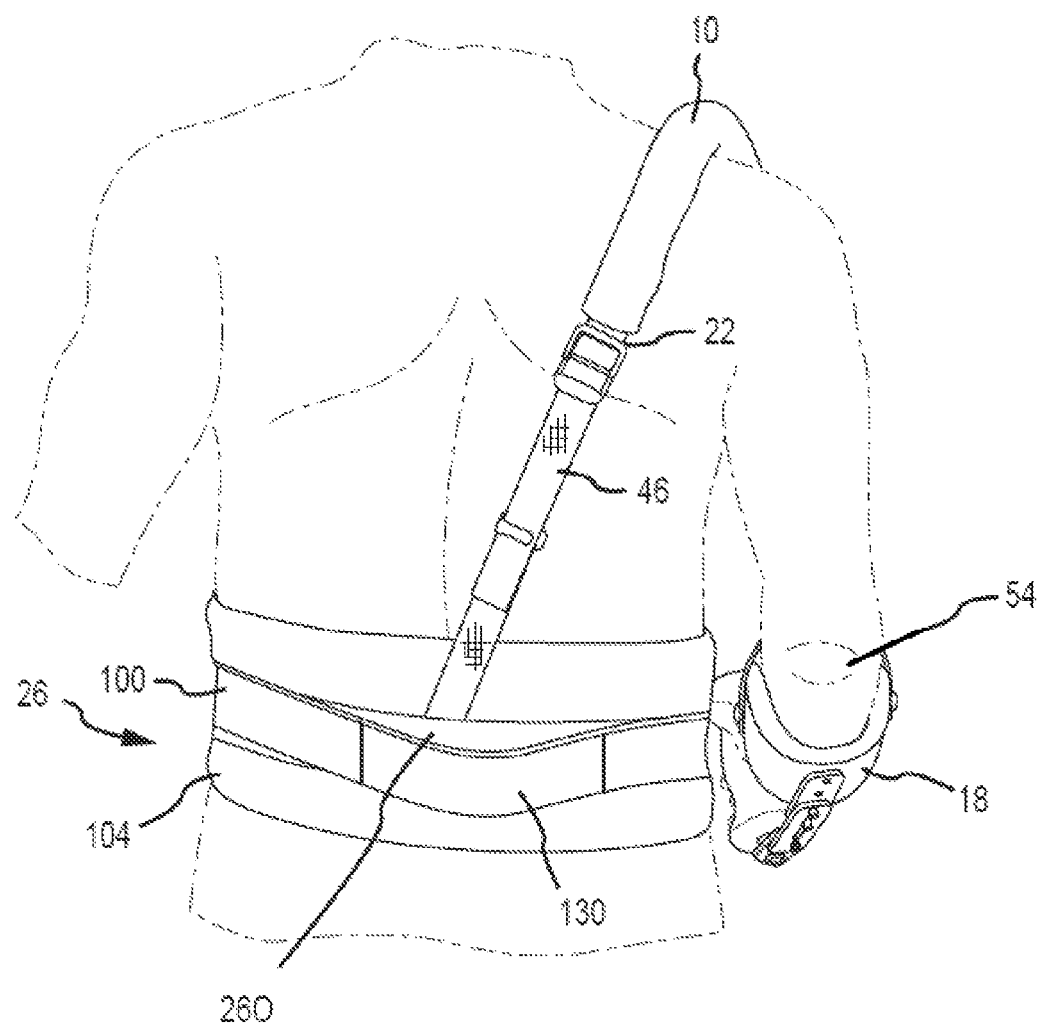
FIG. 4 is a rear elevation view of FIG. 1.
Figure 5:
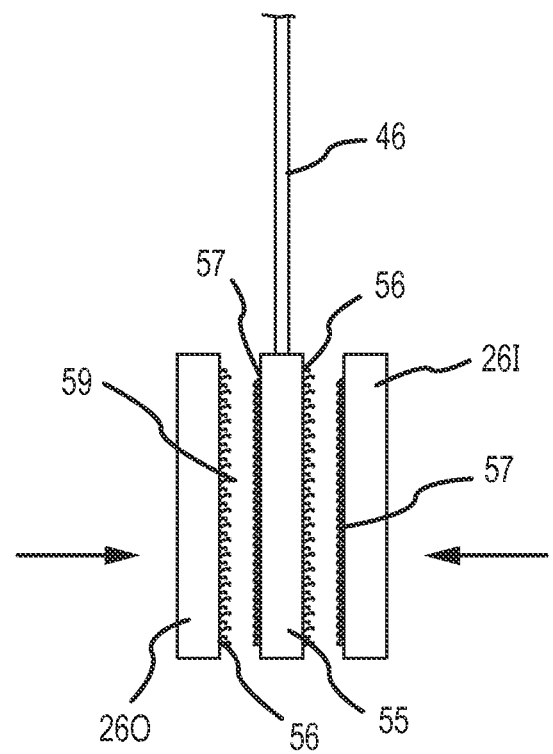
FIG. 5 is a cross-sectional view showing the interconnection between one end of a rear strap of the support and the belt.

Referring now to FIGS. 3-5, a method of interconnecting a rear strap 46 to the belt 26 is shown. More specifically, the rear strap 46 terminates in a fastening member 55 that has a selective interconnection mechanism on each side. For example, in one embodiment of the present invention, a hook and loop fastener is contemplated wherein one side of the fastening member is a loop material 56 and the other side is a hook 57 material. In order to adjust the angle and position of the rear strap 46, and thus the shoulder component 10, an outer portion 26O of the belt is separated from an inner portion 26I of the belt. This provides a gap 59 for the receipt of the connecting member 55. In one embodiment of the present invention, the outer portion 26O of the belt includes a loop material 56 and the inner portion 26I of the belt includes a hook material 57. The connecting member 55 is placed within the gap 59 and the outer portion 26O of the belt and the inner portion 26I of the belt are brought together to capture the connecting member 55. In this way, the corresponding hook/loop surfaces of the connecting member 55, the outer belt member 26O, and the inner belt member 26I fix the position and angle of the rear strap 46. One of skill in the art will appreciate that the relative locations of the hook and loop material is not important. Furthermore, other selective interconnecting mechanisms, such as magnets, snaps, etc. that are well known in the art may be employed instead of hook and loop fasteners. Further, the inner portion 26I of the belt may be a primary belt 100.

In another embodiment of the present invention the primary belt has a plurality of pockets each having a connector for receiving a complimentary connector on the end of the rear strap. Thus, the occupational therapist of the patient may change the angle that the strap and associated shoulder component is positioned on the patient's back. This additional functionality allows for the orientation of the strap and shoulder component to be modified depending on the patient's physical build, for example.

The primary belt 100 or padded belt 104 may also be associated with at least one grasp loop 130 (which may be the outer belt portion 26O). The grasp loop(s) 130 help the occupational therapist in lifting the patient to a standing position or placing them in a sitting position. Further, the grasp loop(s) 130 also help the caregiver guide and stabilize the patient has he or she is conducting therapy.

Figure 6:
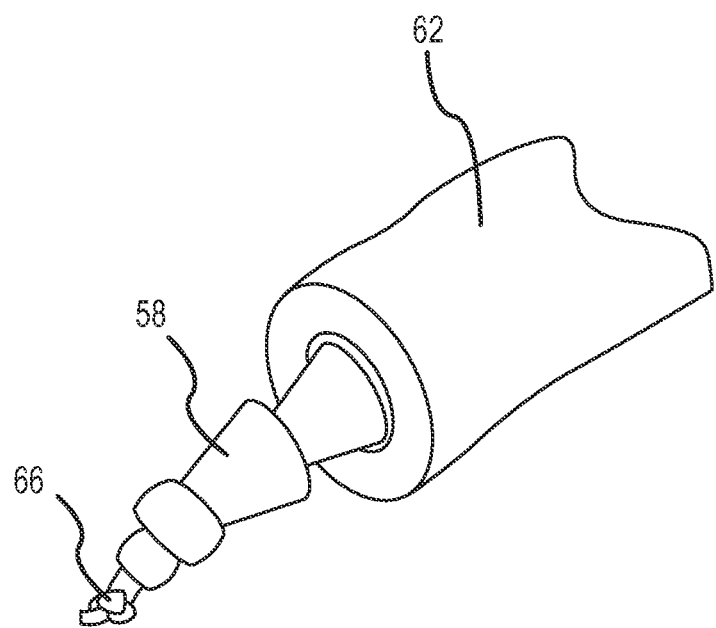
FIG. 6 is a partial perspective view of a shoulder component of one embodiment of the present invention.

Referring now to FIG. 6, instead of thin padded strapping or webbing found in traditional arm straps, one embodiment of the present invention employs an adjustable cushioned member with a core 58 that firmly holds its shape. For example, one embodiment employs Loc-Line® Modular Tube, made by Lockwood, Inc. that is covered with external padding 62 that supports the weight of the arm. By configuring (i.e. flexing) the adjustable core 58, patients can change the path of the shoulder component 10 over the affected shoulder and control the applied pressure. Contact locations on the shoulder can easily be adjusted by repositioning the core 58 whenever desired to shift the load for comfort or to avoid the patient's trapezius altogether. Testing has shown patients particularly enjoy being able to easily move or flex the core 58 to avoid chafing, bruising, and excess contact pressure. This stream-lined simplicity avoids complex harness schemes and is a significant advantage.

The shoulder component shown includes interlocking subcomponents 66 covered with padding 62 that are stiffened by compression. The shoulder component 10 is thus able to selectively bend and hold its position thereby allowing the padded shoulder component 10 to contour to the patient's shoulder, which increases comfort. In some embodiments of the present invention, the shoulder 10 component comprises a tension or bungee cord 66 for facilitating positioning and for providing additional flexibility. An adjustable ladder loc 70 (see FIG. 1, for example,) is incorporated between the shoulder component 10 and front strap 42.

Figure 7:
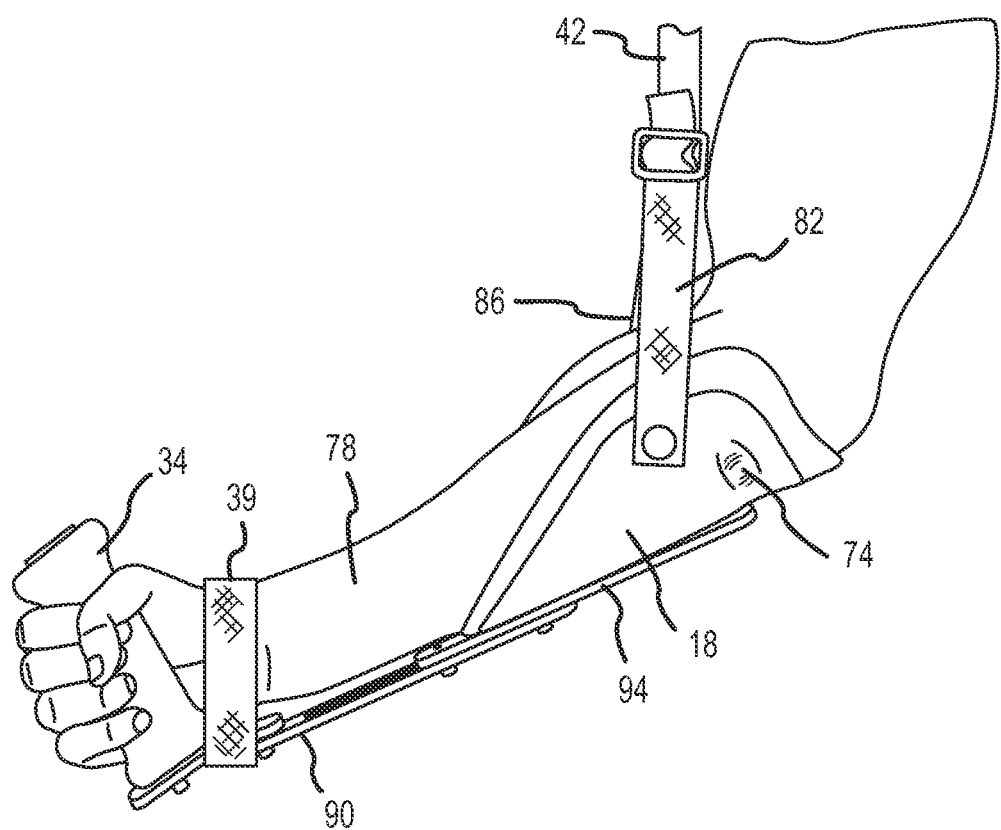
FIG. 7 is a side elevation view showing the patient's arm positioned in an arm cuff of one embodiment of the present invention.
Figure 8:
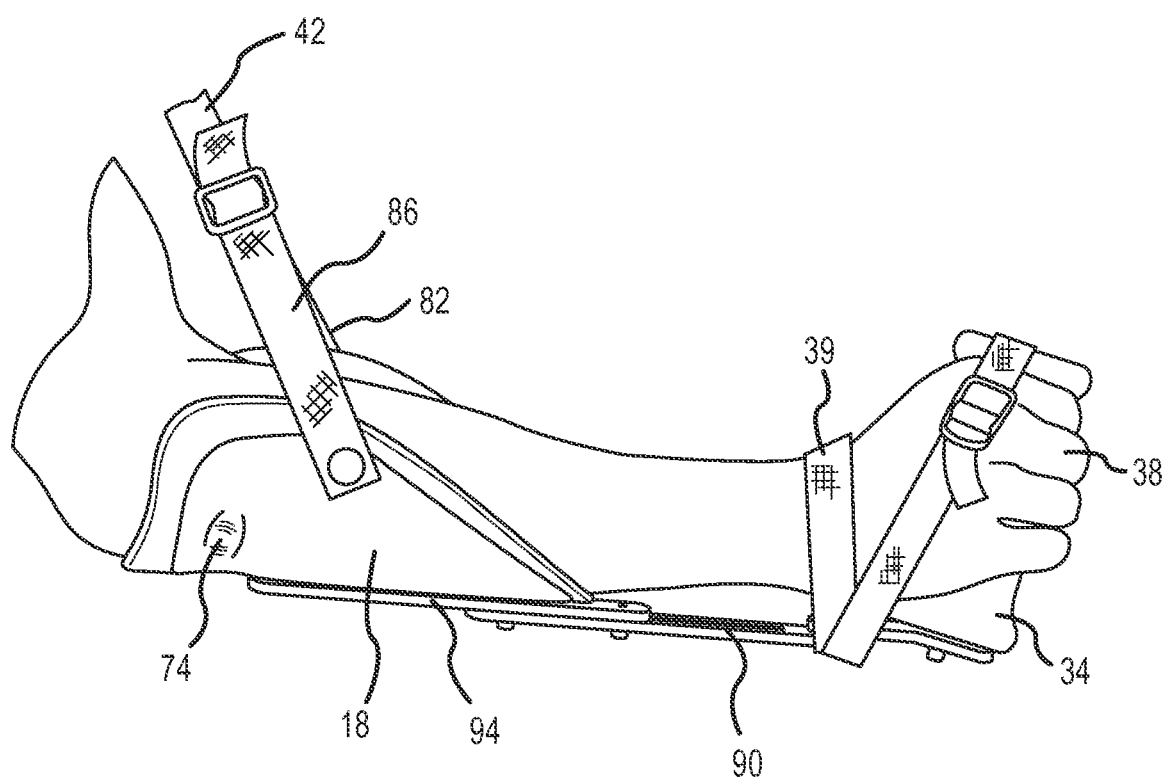
FIG. 8 is a side elevation view opposite to that of FIG. 7.

FIGS. 7 and 8 show a one-piece arm cuff 18 that is preferably molded from KYDEX brand ABS/vinyl sheet plastic. The arm cuff 18 may include indentations 74 that are incorporated into the mold that firmly grasp the patient's lower arm 78 so that the upper arm is lifted into the shoulder joint. The front strap 42 is a medial strap 82 and a lateral strap 86 that attach on either side of the arm cuff 18. The internal/external positions of the lower arm 78 can be altered by adjusting the length of the front strap 42 and/or the lengths of the lateral strap 86 and the medial strap 82. In one embodiment of the present invention, the arm cuff 18 uses snaps or hook and loop attachment members that receive the ends of the lateral strap 86 and the medial strap 82. The arm cuff may also include padding to provide comfort and adjustability required.

The grip 34 is attached to the arm cuff 18 to hold the hand 38 in a specific position. The grip 34 is designed to arrest the patient's hand 38 and to give the patient something to grasp. In one embodiment, the grip 34 is interconnected to a first rigid member 90 that is interconnected to a second rigid member 94 that is attached to the arm cuff 18. The first rigid member 90 may be slidingly and/or rotatably interconnected to the second rigid member 94 so that the distance and/or relative angle between the grip 34 and the arm cuff 18 may be selectively altered. In this way, the caregiver can position the angle of the patient's wrist relative to their arm to increase or decrease wrist flexion. The grip 34 is preferably a tubular member that is over-molded with a soft foam material to accommodate various arm length and positions.

While various embodiments of the present invention have been described in detail, it is apparent that modifications and alterations of those embodiments will occur to those skilled in the art. However, it is to be expressly understood that such modifications and alterations are within the scope and spirit of the present invention, as set forth in the following claims. Further, the invention(s) described herein is capable of other embodiments and of being practiced or of being carried out in various ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

What is claimed is:

1. A support for securing a patient's arm, comprising:
a shoulder component having a first end and a second end;
an arm cuff that is adapted to support the patient's arm, said first end of said shoulder component being associated with said arm cuff;
a hand grip with a restraint that is adapted to wrap about the wrist of the patient, said hand grip interconnected to said arm cuff by a rigid member;
a belt adapted to fit about the waist of the patient;
a back strap having a first end interconnected to said second end of said shoulder component and a second end directly interconnected to said belt; and
where in said first end of said shoulder component is interconnected to said arm cuff by way of an adjustable strap that has a first end directly interconnected to said first end of said shoulder component and a second end directly interconnected to said arm cuff.

2. The support of claim 1, wherein said arm cuff is trough-shaped such that it contours generally to a lower arm of the patient, said arm cuff having an inner wall and an outer wall, wherein at least one of said inner wall and said outer wall includes an indentation that applies pressure to the patient's arm.

3. The support of claim 2, wherein pressure is applied adjacent to the patient's elbow and above the patient's ulna bone.

4. The support of claim 1, wherein said back strap is selectively adjustable in length.

5. The support of claim 1, wherein said belt includes a fastening member that selectively receives a complementary fastening member of said back strap.

6. The support of claim 1, wherein said arm cuff and said hand grip are operably interconnected by a first member, which is interconnected to said arm cuff, to a second member, which is interconnected to said hand grip, said first member interconnected to said second member in a sliding fashion which allows the distance between said arm cuff and said hand grip to be selectively adjusted.

7. The support of claim 1, wherein said shoulder component is comprised of a plurality of interlocked members that are held together by a selectively adjustable tension cord, said interlocked members being overwrapped with a soft, compliant material.

8. The support of claim 1, wherein said arm cuff is elongated having a first intersection and outer section with a lower section therebetween, said intersection and outer section having an indentation position about 1.0 to 1.5 inches from the rear edge of the arm cuff.

9. The support of claim 1, wherein said belt includes attachment points for selectively receiving a first end of said strap; and
wherein said belt is comprised of a primary belt having a first end and a second end, said first end of said belt and said second end of said belt each having complimentary pieces of a buckle, and said secondary belt having a padded portion that is wider than said primary belt.

10. The support of claim 9, wherein the padded portion of said belt is internally supported by a structural stay.

11. The support of claim 1, wherein a combination of said shoulder component and said arm cuff urges the patient's arm upwardly to seat the head of the humerus into the shoulder joint.

12. The support of claim 1 wherein said shoulder component is comprised of interlocking and selectively adjustable interlocking components that are covered with padding.

13. The support of claim 12 wherein said interlocking components are stiffened by elastic compression provided by a cord that runs through at least two of said interlocking components.

14. The support of claim 1 wherein said belt is latched using a seat belt buckle.

15. The support of claim 1 wherein said arm cuff supports a forearm in supination and the wrist in neutral alignment.

16. A support for securing a patient's arm, comprising:
a shoulder component having a first end and a second end;
an arm cuff that is adapted to support the patient's arm, said first end of said shoulder component being associated with said arm cuff;
a hand grip with a restraint that is adapted to wrap about a wrist of the patient, said hand grip interconnected to said arm cuff by a rigid member;
a belt adapted to fit about a waist of the patient;
a back strap having a first end interconnected to said second end of said shoulder component and a second end selectively interconnected to said belt;
wherein said hand grip is interconnected to said arm cuff by an articulating mechanism, a first portion thereof being interconnected to said hand grip and a second portion thereof being interconnected to said arm cuff wherein said first portion and said second portion being able to articulate and lock relative to each other; and
wherein said belt includes a fastening member that selectively receives a complementary fastening member of said back strap.

17. A support for securing a patient's arm, comprising:
a shoulder component having a first end and a second end;
an arm cuff that is adapted to support the patient's arm, said first end of said shoulder component being associated with said arm cuff;
a hand grip with a restraint that is adapted to wrap about a wrist of the patient, said hand grip interconnected to said arm cuff by a rigid member;
a belt adapted to fit about a waist of the patient;
a back strap having a first end interconnected to said second end of said shoulder component and a second end selectively interconnected to said belt; and
wherein said arm cuff is interconnected to said shoulder component via a lateral strap and a medial strap, said lateral strap and medial strap being selectively adjustable.

* * * * *